(12) United States Patent
Nakajima et al.

(10) Patent No.: US 9,289,333 B2
(45) Date of Patent: Mar. 22, 2016

(54) DISPOSABLE DIAPER USING ELASTIC SHEETS

(75) Inventors: Kaiyo Nakajima, Kanonji (JP); Toshimitsu Baba, Kanonji (JP); Ryuichi Kamiyama, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 844 days.

(21) Appl. No.: 13/260,781

(22) PCT Filed: Mar. 30, 2010

(86) PCT No.: PCT/JP2010/002294
§ 371 (c)(1),
(2), (4) Date: Sep. 28, 2011

(87) PCT Pub. No.: WO2010/113472
PCT Pub. Date: Oct. 7, 2010

(65) Prior Publication Data
US 2012/0016334 A1    Jan. 19, 2012

(30) Foreign Application Priority Data

Mar. 30, 2009  (JP) ................................ 2009-083629

(51) Int. Cl.
*A61F 13/15*  (2006.01)
*A61F 13/20*  (2006.01)
(Continued)

(52) U.S. Cl.
CPC ......... *A61F 13/496* (2013.01); *A61F 13/49011* (2013.01); *A61F 13/49014* (2013.01); *A61F 13/49017* (2013.01)

(58) Field of Classification Search
CPC ...................... A61F 13/49007–13/4902; A61F 2013/49007–2013/4902; A61F 2013/49025–2013/49028

USPC ................. 604/367, 385.01, 385.03, 385.22, 604/385.24–385.25, 385.27, 385.31, 604/386–387
See application file for complete search history.

(56) References Cited

U.S. PATENT DOCUMENTS 4,743,241 A * 5/1988 Igaue et al. ............... 604/385.26
5,242,436 A * 9/1993 Weil et al. ................ 604/385.29
(Continued)

FOREIGN PATENT DOCUMENTS

EP          1547558 A1    6/2005
EP          1614407 A2    1/2006
(Continued)

OTHER PUBLICATIONS

Supplementary European Search Report dated Nov. 14 2013, corresponds to European patent application No. 10758252.0.
(Continued)

*Primary Examiner* — Michele M Kidwell
(74) *Attorney, Agent, or Firm* — Hauptman Ham, LLP (57) ABSTRACT

A disposable diaper using elastic sheet materials so that a contact surface pressure may be locally enhanced and thereby the diaper may be prevented from being noticeably displaced on the wearer's body during used thereof is provided. Of first and second waist regions at least the first waist region is contractible. The first waist region includes waist auxiliary elastic sheets extending in a direction of a transverse axis between opposite side edges of the first waist region and leg auxiliary elastic sheets extending along front peripheral edges of leg-openings. The waist auxiliary elastic sheets and the leg auxiliary elastic sheets overlap one another in areas of the opposite side edges of the first waist region adjacent to the leg-openings respectively. With the diaper put on the wearer's body, these areas come in contact with upper lateral regions of the wearer's iliac bones inclusive of the vicinity thereof.

19 Claims, 4 Drawing Sheets

(51) Int. Cl.
*A61F 13/496* (2006.01)
*A61F 13/49* (2006.01)

(56) References Cited

U.S. PATENT DOCUMENTS

| | | | | |
|---|---|---|---|---|
| 5,407,438 | A | * | 4/1995 | Hedlund et al. ......... 604/385.26 |
| 5,464,401 | A | * | 11/1995 | Hasse et al. .............. 604/385.25 |
| 5,899,896 | A | * | 5/1999 | Suprise et al. ................ 604/391 |
| 6,149,637 | A | * | 11/2000 | Allen et al. .................. 604/366 |
| 6,613,033 | B1 | | 9/2003 | Popp et al. |
| 6,652,504 | B1 | * | 11/2003 | Olson et al. .............. 604/385.25 |
| 7,118,558 | B2 | * | 10/2006 | Wu et al. .................. 604/385.29 |
| 7,918,840 | B2 | | 4/2011 | Corneliusson ........... 604/385.28 |
| 8,092,440 | B2 | * | 1/2012 | Hermansson et al. ... 604/385.27 |
| 2003/0114817 | A1 | * | 6/2003 | Roessler et al. .............. 604/378 |
| 2006/0271009 | A1 | * | 11/2006 | Cartier et al. ............ 604/385.31 |
| 2008/0021430 | A1 | * | 1/2008 | Back .......................... 604/385.3 |
| 2008/0269711 | A1 | * | 10/2008 | Sasayama et al. ....... 604/385.09 |
| 2008/0300568 | A1 | * | 12/2008 | Fujioka et al. .......... 604/385.27 |
| 2010/0286646 | A1 | * | 11/2010 | Takino et al. .............. 604/385.3 |

FOREIGN PATENT DOCUMENTS

| | | |
|---|---|---|
| JP | 2004-520861 A | 7/2004 |
| JP | 2006-043015 A | 2/2006 |
| JP | 2006-280468 A | 10/2006 |

OTHER PUBLICATIONS

International Search Report for PCT/JP2010/002294 mailed Jul. 13, 2010.

* cited by examiner

DISPOSABLE DIAPER USING ELASTIC SHEETS

RELATED APPLICATIONS

The present application is a National Phase of International Application Number PCT/JP2010/002294, filed Mar. 30, 2010 and claims priority from, Japanese Application Number 2009-083629, filed Mar. 30, 2009.

TECHNICAL FIELD

The present disclosure relates to disposable diapers and particularly to disposable diapers using sheet-like elastic members.

BACKGROUND

It is known to use elastic members providing a desired contact surface pressure for a diaper in order to improve fit to the wearer's body and to prevent body waste from leaking sideways from the diaper. For example, JP 2006-43015 A discloses a disposable diaper provided in front and rear waist regions with strand-like waist elastic elements extending in a transverse direction and strand-like leg elastic elements extending along peripheral edges of the leg-openings.

According to JP 2006-43015 A, the waist regions are provided with a plurality of strand-like waist elastic elements to improve fit of these waist regions to the wearer's body and a plurality of strand-like leg elements provided along the peripheral edges of the respective leg-openings to prevent body waste from leaking sideways from the diaper.

To prevent the diaper from being displaced on the wearer's body during use thereof, a predetermined or higher level of a contact surface pressure is required for the waist elastic elements. However, if the waist elastic elements evenly provide a relatively high contact surface pressure, the wearer often may feel a tightening in his or her waist as a whole, experience an oppressive feeling and/or have a surface imprint in a relatively soft region of his or her skin particularly when strand-like elastic members are used as the waist elastic elements.

CITATION LIST

Patent Literature

[PTL 1]
Japanese Patent Application Laid-Open Publication No. 2006-43015 A

SUMMARY

A disposable diaper according to one or more embodiment of the present invention has a longitudinal axis, a transverse axis extending orthogonally to the longitudinal axis, a skin-facing side and a non-skin-facing-side opposite to the skin-facing side, and comprises a first waist region, a second waist region, a crotch region extending between said first and second waist regions, a waist-opening and a pair of leg-openings. At least the first waist region of the first and second waist regions of the above disposable diaper is elastically contractile. In this diaper, the first waist region is provided between opposite side edges thereof with at least one waist auxiliary elastic sheet extending in a direction of the transverse axis, and leg auxiliary elastic sheets extending along front peripheral edges of the respective leg-openings. The at least one waist auxiliary elastic sheet and the leg auxiliary elastic sheets directly or indirectly overlap one another at regions defined between the opposite side edges of the first waist region adjacent to the leg-openings.

DETAILED DESCRIPTION

Figure 1:
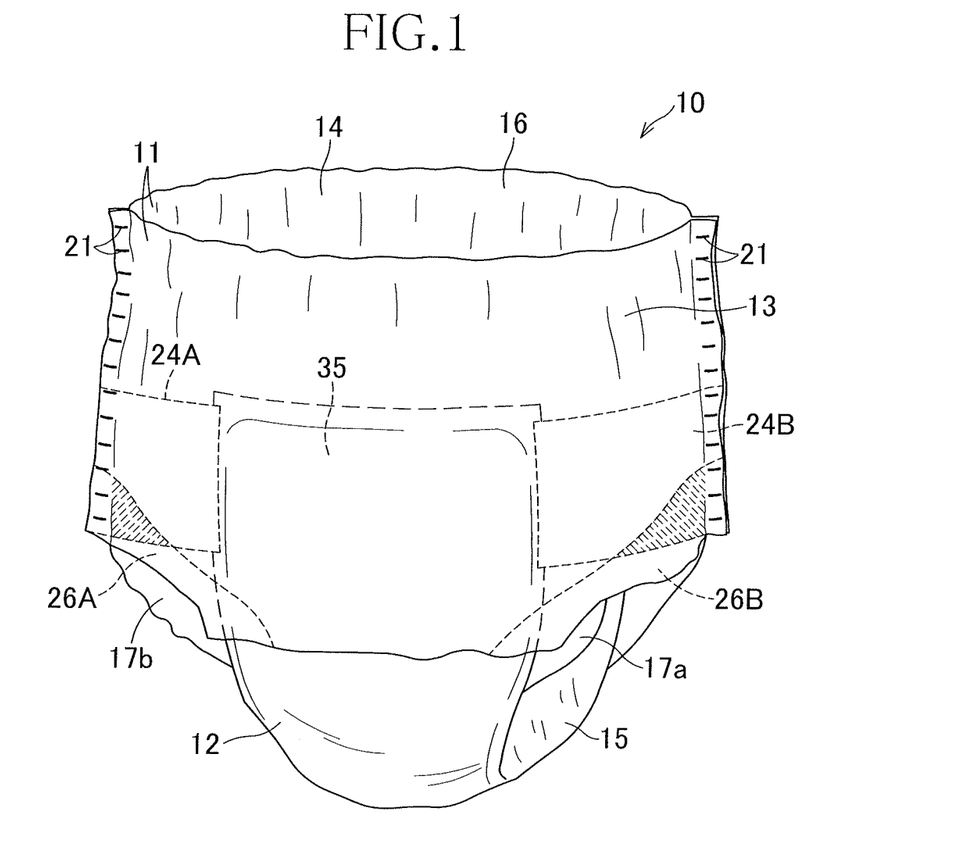
FIG. 1 is a perspective view of a disposable diaper in accordance with one or more embodiments.
Figure 2:
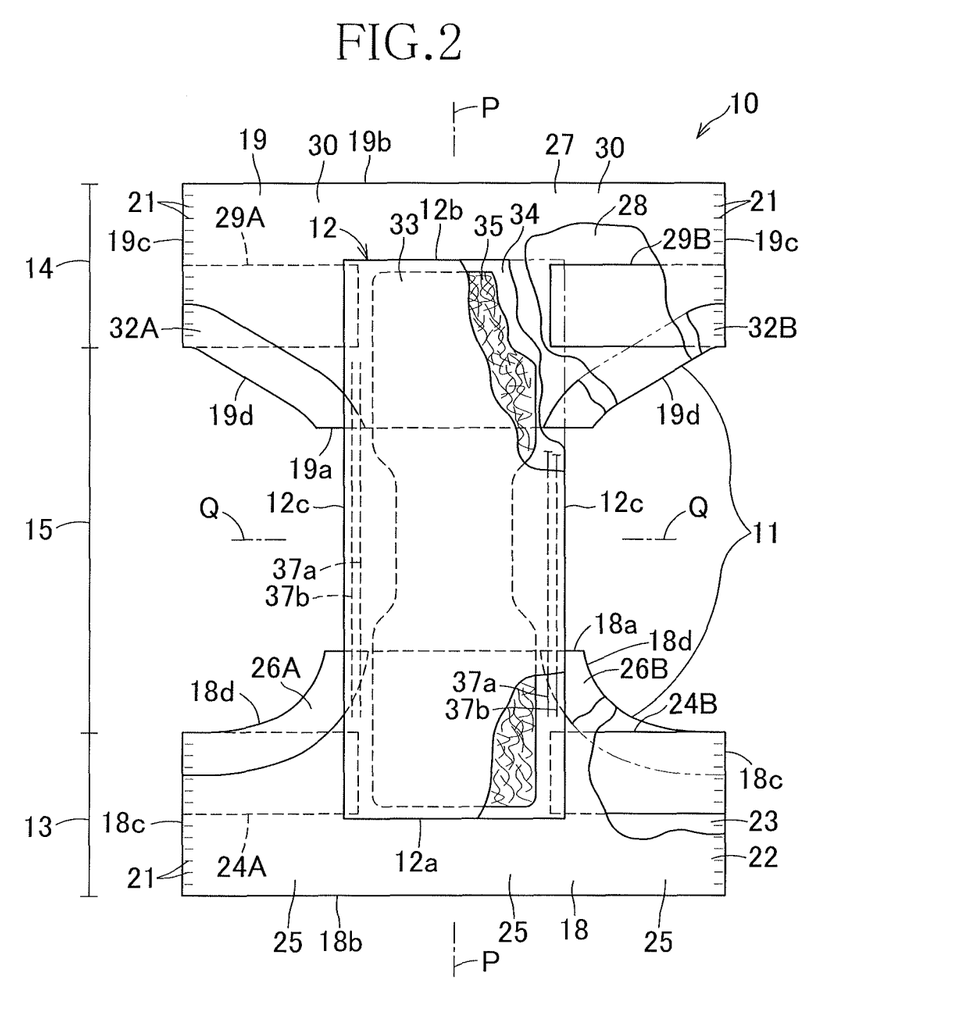
FIG. 2 is a partially cutaway plan view of the diaper in its flatly developed state.

Details of a disposable diaper according to exemplary embodiments of the present invention will be more fully understood from the description given hereunder in reference to the accompanying drawings. It should be appreciated that same or similar reference numerals used in the specification designate same or similar members or regions through all specifically disclosed embodiments. A diaper 10 in accordance with one or more embodiments is illustrated in FIGS. 1 and 2. As shown in FIGS. 1 and 2, the diaper 10 has a longitudinal axis P, a transverse axis Q being orthogonal to the longitudinal axis P, a skin-facing side, a non-skin-facing side opposite to the skin-facing side, an annular waist panel 11, an absorbent chassis 12 attached to the inner surface, i.e., the skin-facing side of the annular waist panel 11, a front waist region 13, a rear waist region 14 and a crotch region 15 extending between the front and rear waist regions 13, 14, a waist-opening 16 and a pair of leg-openings 17a, 17b.

The annular waist panel 11 comprises a front waist panel 18 defining the front waist region 13 and a front part of the crotch region 15, and a rear waist panel 19 defining the rear waist region 14 and a rear part of the crotch region 15.

The front waist panel 18 is contoured by an inner end 18a extending in a direction of the transverse axis Q, an outer end 18b opposed to the inner end 18a in a direction of the longitudinal axis P and extending in a direction of the transverse axis Q, opposite outer side edges 18c, 18c (corresponding to opposite side edges of the front waist region) extending from the outer end 18b toward the crotch region 15 in the direction of the longitudinal axis P, and opposite inner side edges 18d, 18d (corresponding to the front peripheral edges of the leg-openings) extending inward from the respective outer side edges 18c, 18c obliquely with respect to the direction of the longitudinal axis P so as to describe inwardly concave curves.

The rear waist panel 19 is contoured by an inner end 19a extending in the direction of the transverse axis Q, an outer end 19b opposed to the inner end 19a in a direction of the longitudinal axis P, opposite outer side edges 19c, 19c (corresponding to opposite side edges of the rear waist region) extending from the outer end 19b toward the crotch region 15 in the direction of the longitudinal axis P, and opposite inner side edges 19d, 19d (corresponding to the rear peripheral edges of the leg-openings) extending inward from the respective outer side edges 19c, 19c obliquely with respect to the direction of the longitudinal axis P so as to describe inwardly concave curves.

The opposite side edges 18c, 18c of the front waist panel 18 and the opposite side edges 19c, 19c of the rear waist panel 19 are joined together in side seams 21 arranged intermittently in the direction of the longitudinal direction P by known means such as hot embossing or ultrasonic sealing.

The front waist panel 18 comprises a first elastic sheet 22 lying on the skin-facing side and a first non-elastic sheet 23 lying on the non-skin-facing side. The first elastic sheet 22 is formed of an elastically stretchable and contractible fibrous non-woven fabric, an elastically stretchable and contractible plastic sheet or a laminate thereof. The first non-elastic sheet 23 is formed of a fibrous non-woven fabric which is neither elastically stretchable nor elastically contractible, a plastic sheet which is neither elastically stretchable nor elastically contractible, or a laminate thereof. The front waist panel 18 further comprises a pair of front waist auxiliary elastic sheets 24A, 24B sandwiched between the first elastic sheet 22 and the first non-elastic sheet 23 and bonded to these two sheets 22, 23 by hot melt adhesive.

These paired front waist auxiliary elastic sheets 24A, 24B are elastically contractible at least in the direction of the transverse axis Q and provided on opposite lateral regions 25, 25 of the front waist region 13 so as to be symmetric about the longitudinal axis P and spaced from each other in the direction of the transverse axis Q by a predetermined distance. It should be appreciated that it is possible to replace these front waist auxiliary elastic sheets 24A, 24B by a single elastic sheet continuously extending in the direction of the transverse axis Q between the opposite side edges 18c, 18c of the front waist region 13.

Front leg auxiliary elastic sheets 26A, 26B which are smaller than the front waist auxiliary elastic sheets 24A, 24B in width are attached to the skin-facing side of the first elastic sheet 22 by hot melt adhesive so as to extend along the front peripheral edges 18d, 18d of the leg-openings defined by the front waist panel 18.

The rear waist panel 19 comprises a second elastic sheet 27 lying on the skin-facing side and a second non-elastic sheet 28 lying on the non-skin-facing side. The second elastic sheet 27 is formed of an elastically stretchable and contractible fibrous non-woven fabric, an elastically stretchable and contractible plastic sheet or a laminate thereof. The second non-elastic sheet 28 is formed of a fibrous non-woven fabric which is neither elastically stretchable nor elastically contractible, a plastic sheet which is neither elastically stretchable nor elastically contractible, or a laminate thereof. The rear waist panel 19 further comprises a pair of rear waist auxiliary elastic sheets 29A, 29B sandwiched between the second elastic sheet 27 and the second non-elastic sheet 28 and bonded to these two sheets 27, 28 by hot melt adhesive.

These paired rear waist auxiliary elastic sheets 29A, 29B are elastically contractible at least in the direction of the transverse axis Q and provided on opposite lateral regions 30, 30 of the rear waist region 14 so as to be symmetric about the longitudinal axis P and spaced from each other in the direction of the transverse axis Q by a predetermined distance. It should be appreciated that it is possible to replace these rear waist auxiliary elastic sheets 29A, 29B by a single elastic sheet continuously extending in the direction of the transverse axis Q between the opposite side edges 19c, 19c of the rear waist region 14.

Rear leg auxiliary elastic sheets 32A, 32B, which are smaller than the rear waist auxiliary elastic sheets 29A, 29B in width, are attached to the skin-facing side of the second elastic sheet 27 by hot melt adhesive so as to extend along the rear peripheral edges 19d, 19d of the leg-openings defined by the rear waist panel 19.

The front and rear waist auxiliary elastic sheets 24A, 24B, 29A, 29B as well as the front and rear leg auxiliary elastic sheets 26A, 26B, 32A, 32B may be formed from various stock materials such as an elastically stretchable and contractible fibrous non-woven fabric sheet, an elastically stretchable and contractible plastic film, a laminate of these fibrous non-woven fabric sheet and plastic film, or an elastic sheet made from natural rubber. These auxiliary elastic sheets are bonded to the associated members under tension corresponding to a stretch ratio in a range of about 1.5 to 3.5 with respect to the non-stretched state. In some embodiments, the elastically stretchable and contractible fibrous non-woven fabric sheet is formed of (A) an elastically stretchable non-woven fabric made of elastic fibers, such as urethane elastic fibers, or (B) an elastically stretchable non-woven fabric made of elastically stretchable fibers mixed with non-elastically stretchable thermoplastic synthetic fibers. In other embodiments, a plurality of rubber strings can be used as the leg elastic members.

The first and second elastic sheets 22, 27 may be obtained by mechanically drawing a non-woven fabric formed from mixed fibers of elastomer fibers and thermoplastic fibers, which are neither elastically stretchable nor elastically contractible, using the known drawing means such as, for example, a pair of gear rolls. These first and second elastic sheets 22, 27 are respectively bonded to the first and second non-elastic sheets 23, 28 preferably under tension corresponding to a stretch ratio in a range of about 1.5 to 3.0 in the direction of the transverse axis Q with respect to the non-stretched state.

The elastomer fibers used for the first and second elastic sheets 22, 27 may be urethane- or polyethylene-based fibers and have a mixing rate preferably in a range of 20 to 75% by mass of all mixed fibers of the non-woven fabric. This is for the reason that if the mixing rate of the elastomer fibers is 20% by mass or lower, the mixing rate of the thermoplastic fibers will be undesirably excessive and the elastic sheets will be apt to get distorted, and if the mixing rate of the elastomer fibers is 75% by mass or higher, the sheets as a whole will be apt to become icky and to create a discomfortable feeling to the wearer.

The absorbent chassis 12 has a vertically long rectangular shape contoured by a front end 12a extending in the direction of the transverse axis Q, a rear end 12b opposed to the front end 12a in the direction of longitudinal axis P and extending in the direction of the transverse axis Q, and opposite side edges 12c, 12c extending in the direction of the longitudinal axis P between the front and rear ends 12a, 12b.

The absorbent chassis 12 includes a liquid-pervious inner sheet 33 lying on the skin-facing side, a liquid-impervious outer sheet 34 lying on the non-skin-facing side and a liquid-absorbent core 35 formed from a mixture of fluff pulp fibers and super-absorbent polymer particles and sandwiched between the inner sheet 33 and the outer sheet 34. The liquid-absorbent core 35 is previously shaped in a desired shape such as, for example, a panel and may be entirely wrapped with a liquid-dispersant sheet (not shown).

The inner sheet 33 and the outer sheet 34 extend outward beyond a periphery of the liquid-absorbent core 35 and bonded together outboard of the liquid-absorbent core 35 by hot melt adhesive so as to define a pair of side flaps extending in the direction of the longitudinal axis P outward beyond the opposite side edges of the liquid-absorbent core 35 as viewed in the direction of the transverse axis Q, and a pair of end flaps extending in the direction of the transverse axis Q outboard of the front and rear ends of the liquid-absorbent core 35 as viewed in the direction of the longitudinal axis P. The end flaps are bonded to respective inner surfaces of the front and rear waist panels 18, 19 by hot melt adhesive so that the absorbent chassis 12 may be suspended from the annular waist panel 11 when the diaper 10 is worn (See FIG. 1).

The side flaps are respectively provided with elastic strands or thread elements 37a, 37b extending in the direction of the longitudinal axis P. The side flaps may be respectively provided with barrier cuffs (not shown) formed of separately prepared liquid-impervious sheet materials or formed by enlarging the outer sheet 34 so as to extend further in the direction of the transverse axis Q beyond the top-sheet 33 and folding back the outer sheet 34. Such barrier cuffs can serve to prevent bodily fluids from leaking out sideways.

As will be apparent from FIG. 2, the liquid-absorbent core 35 extends across the crotch region 15 into the respective middle zones of the front and rear waist regions 13, 14 in the direction of the longitudinal axis P. The front waist auxiliary elastic sheets 24A, 24B and the rear waist auxiliary elastic sheets 29A, 29B intersect with the side flaps of the absorbent chassis 12 but not with the side edges of the liquid-absorbent core 35.

With the arrangement as has been described above, the contact surface pressure provided by the front and rear waist auxiliary elastic sheets 24A, 24B, 29A, 29B further assures to put the absorbent chassis 12 in close contact with the wearer's skin but such a contact surface pressure is not exerted directly on the liquid-absorbent core. Consequently, the liquid-absorbent core 35 would not be formed with gathers tending to disturb its liquid-absorption capacity.

While the front and rear waist regions 13, 14 are provided with the respective waist auxiliary elastic sheets and the respective leg auxiliary elastic sheets in the embodiment particularly illustrated in FIGS. 1 and 2, the desired effect can be achieved so far as at least one of the front and rear waist regions 13, 14 is provided with such an arrangement of the auxiliary elastic sheets. While the front and rear waist regions 13, 14 are defined by the separate front and rear waist panels 18, 19 according to this embodiment, it is also possible to form these waist regions 13, 14 by a single continuous sheet material so as to define the outer surface of the diaper 10. In such a diaper, it is also possible to provide the front and rear leg auxiliary elastic sheets 26A, 26B continuously along the peripheral edges of the leg-openings through the front peripheral edges to the rear peripheral edges, respectively.

Figure 3:
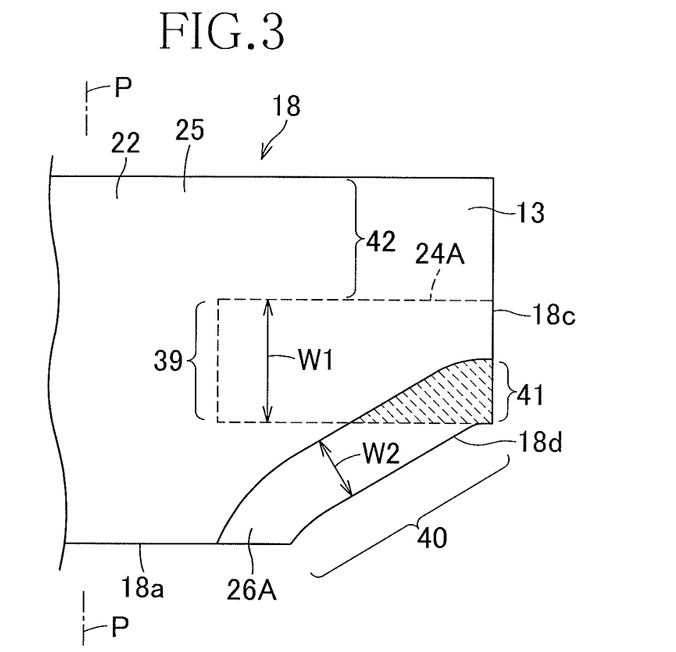
FIG. 3 is an enlarged partial view of a front waist panel of the diaper.

The diaper 10 is partially shown in a larger scale in FIG. 3. In this embodiment, the front waist panel 18 is shaped symmetrically about the longitudinal axis P and the arrangement of the rear waist panel 19 is also substantially similar to the front waist panel 18 as has previously been described with respect to FIGS. 1 and 2. In view of this, the rear waist panel 19 and the absorbent chassis 12 are not shown in FIG. 3 for the sake of simplicity.

The front waist panel 18 includes a first elastic region 39 in which the front waist auxiliary elastic sheet 24A is provided, a second elastic region 40 in which the front leg auxiliary elastic sheet 26A is provided, a third elastic region (indicated by dashed lines) in which the front waist auxiliary elastic sheet 24A overlapping the front leg auxiliary elastic sheet 26A, and a fourth elastic region 42 including neither the front waist auxiliary elastic sheet 26A nor the front leg auxiliary elastic sheet 26A and extending in the direction of the transverse axis Q between the peripheral edge of the waist-opening and the first elastic region 39.

The third elastic region 41 is the region in which the first elastic region 39 and the second elastic region 40 indirectly overlap each other, i.e., through the intermediary of the first elastic sheet 22, in other words, the region in which the front waist auxiliary elastic sheet 24A and the front leg auxiliary elastic sheet 26A indirectly intersect with each other. Thus a contact surface pressure is higher in the third elastic region 41 than in the first elastic region 39 and in the second elastic region 40. The fourth elastic region 42 includes neither the front waist auxiliary elastic sheet 24A nor the front leg auxiliary elastic sheet 26A and is subject only to a contact surface pressure provided by the first elastic sheet 22. As a consequence, the contact surface pressure in the fourth elastic region 42 is lower than the contact surface pressure in the first and second elastic regions 39, 40.

Thus the contact surface pressures (refer to as "Pressure") in the first-fourth elastic regions 39, 40, 41, 42 may be correlated one with another as follows:

"Pressure" in the third elastic region 41 is higher than that in the second elastic region 40;

"Pressure" in the second elastic region 40 is higher than or equal to that in the first elastic region 39; and "Pressure" in the first elastic region 39 is higher than that in the fourth elastic region 42.

More specifically, the contact surface pressure in the fourth elastic region 42 is preferably in a range of about 30 to 70 g/cm$^2$. The contact surface pressure and the tensile stress are sufficiently lower in the fourth elastic region 42 than in the other elastic regions to assure that the diaper 10 can be smoothly put on the wearer's body merely by easily enlarging the waist-opening.

In the first elastic region 39, the first elastic sheet 22 cooperates with the front waist auxiliary elastic sheet 24A to provide the contact surface pressure preferably in a range of about 60 to 100 g/cm$^2$. In the second elastic region 40, the first elastic sheet 22 cooperates with the front leg auxiliary elastic sheet 26A to provide the contact surface pressure preferably in a range of about 70 to 120 g/cm$^2$.

To prevent body waste from leaking beyond the front peripheral edge 18d of the leg-opening, the second elastic region 40 preferably has the contact surface pressure higher than the contact surface pressure in the first elastic region 30 which serves to assure appropriate fit of the front waist region 13 to the wearer's body. Since both the front waist auxiliary elastic sheet 24A and the front leg auxiliary elastic sheet 26A are formed, ad litteram, by elastic sheet materials, these sheets 24, 26A would not provide a locally high contact surface pressure and leave compression marks on the wearer's skin, unlike diapers having elastic strands or thread members.

In the third elastic region 41, the first elastic sheet 22, the front waist auxiliary elastic sheet 24A and the front leg auxiliary elastic sheet cooperate together to generate the contact surface pressure preferably in a range of about 140 to 230 g/cm$^2$ to provide for a desired effect as will be described later.

Figure 4:
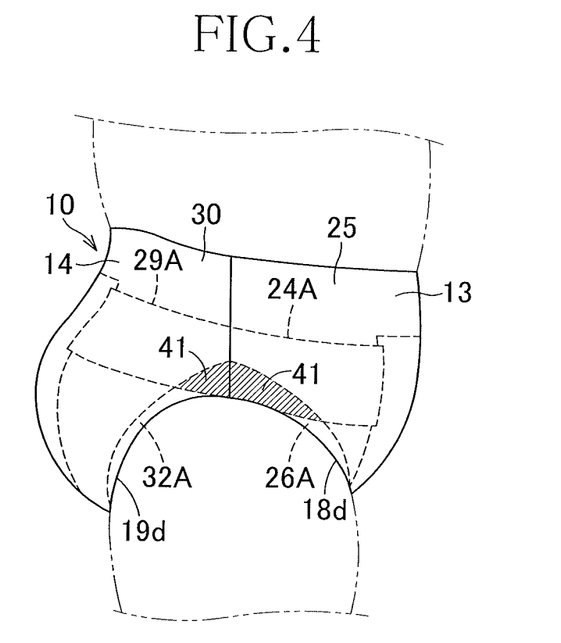
FIG. 4 illustrates the diaper put on the wearer's body.

As will be appreciated from FIG. 4, the third elastic region 41 defined by the front waist auxiliary elastic sheet 24A and the front leg auxiliary elastic sheet 26A in the front waist region 13 and the third elastic region 41 defined by the rear waist auxiliary elastic sheet 29A and the rear leg auxiliary elastic sheet 32A in the rear waist region 14 are adapted to oppose the upper lateral region of the wearer's iliac bone (or iliac crest) and/or the vicinity thereof when the diaper 10 is put on the wearer's body.

In general, the upper lateral region of the wearer's iliac bone and the vicinity thereof are relatively free from the movement of the wearer's belly and legs and, even when the wearer walks or crawls on his or her belly, the positions of the upper lateral region of the wearer's iliac bone and the vicinity thereof are practically not affected by such movement of the wearer.

In view of this, the third elastic region 41 generating the highest contact surface pressure among the first through fourth elastic regions may be positioned on the upper lateral region of the wearer's iliac bone and/or the vicinity thereof which is practically not affected by the wearer's movement to stabilize the third elastic region 41 in close contact with this region of the wearer.

The third elastic region 41 of the front waist region 13 is subjected to, in addition to the contact surface pressure generated from cooperation of the front waist auxiliary elastic sheet 24A lying on the lateral region 25 of the front waist region 13 and the front leg auxiliary elastic sheet 26A extending along the front peripheral edge 18d of the leg-opening, the tensile stress of the rear waist auxiliary elastic sheet 29A lying on the lateral region 30 of the rear waist region 14 and the auxiliary elastic sheet 32A extending along the rear peripheral edge 19d of the leg-opening so as to be entirely put in close contact with the upper lateral region of the wearer's iliac bone inclusive of the vicinity thereof. In this way, the diaper 10 is locally but planarly immobilized on the most stable region around the wearer's waist and a displacement of the diaper 10 put on the wearer's body is effectively prevented.

Depending on a size of the product, a width dimension W1 of the front waist auxiliary elastic sheet 24A may be preferably about 10 mm or larger or about 50% or more of a length dimension of the side edge 18c of the front waist region 13, and a width dimension W2 of the front leg auxiliary elastic sheet 26A may be preferably about 5 mm or larger to obtain the third elastic region 41 assuring the above-described effect.

Provided that these dimensional requirements are met, the third elastic region 41 can be defined so as to be reliably positioned on the upper lateral region of the wearer's iliac bone inclusive of the vicinity thereof even if there is more or less individual variability of the iliac bone's position due to factors such as the personal difference in body height. If the width dimension W1 of the front waist auxiliary elastic sheet 24A is about 10 mm or less or if the width dimension W2 of the front leg auxiliary elastic sheet 26A is 5 mm or less, the contact surface pressure of the respective elastic sheets might be locally exerted on the wearer's skin leading to an oppressive feeling against the wearer and/or leave compression marks on the wearer's skin.

It is possible to form the front leg auxiliary elastic sheet 26A so as to be tapered from the outer side edge 18c to the inner end 18a of the front waist region 13 (i.e., toward the crotch region) so far as the zone of the front leg auxiliary elastic sheet 26A overlapping the front waist auxiliary elastic sheet 24A has the width dimension W2.

While the front waist auxiliary elastic sheet 24A indirectly overlaps the front leg auxiliary elastic sheet 26A through the intermediary of the first elastic sheet 22 in the third elastic region 41 so far as the illustrated embodiment is concerned, it is also possible to sandwich both the front leg auxiliary elastic sheet 26A and the front waist auxiliary elastic sheet 24A between the first elastic sheet 22 and the first non-elastic sheet 23 so as to overlap each other in a direct manner. With such an arrangement of the front waist auxiliary elastic sheet 24A and the front leg auxiliary elastic sheet 26A directly overlapping each other, these two sheets 24A, 26A may be bonded to each other by hot melt adhesive or may be not bonded to each other at all.

The contact surface pressure in the first-fourth elastic regions 39, 40, 41, 42 may be measured, for example, by a method as will be described below.

Example

The diaper 10 in accordance with an exemplary embodiment (e.g., an L-size diaper for children, a product of the applicant, Uni-Charm corporation) is put on a doll for measurement of the contact surface pressure and the contact surface pressure in each of the first-fourth elastic regions 39, 40, 41, 42 is measured. The doll, also a product of the applicant, Uni-Charm corporation, is made from acrylic resin and has a circumferential dimension of 450 mm around the waist and a circumferential dimension of 525 mm around the buttocks.

Equipment

For measurement of the contact surface pressure, "Contact Surface Pressure Measuring System" (manufactured by AMI TECHNO CO., LTD. in Japan, with a circular contact shoe having a diameter of 15 mm, and a measurement unit in g/cm$^2$) was used.

Comparative Example

An ordinary diaper (e.g., an L-size diaper for children, a product of the applicant, Uni-Charm corporation) including none of the first-fourth elastic regions 39, 40, 41, 42 was used as a Comparative Example, and a contact surface pressure in regions corresponding to the first-fourth elastic regions of Example was measured.

Results

The result of measurement (average value calculated from five actual measurement values for each region) under the conditions for measurement as have been described above are listed in TABLE 1.

TABLE 1

|  | Contact surface pressure in first elastic region 39 | Contact surface pressure in second elastic region 40 | Contact surface pressure in third elastic region 41 | (unit: g/cm$^2$) Contact surface pressure in fourth elastic region 42 |
| --- | --- | --- | --- | --- |
| Example 1 | 68 | 71 | 183 | 49 |
| Comparative Example | 29 | 68 | 128 | 66 |

As will be apparent from the measurement result listed above, a relationship of the contact surface pressure among the first-fourth elastic regions 39, 40, 41, 42 in Example is as follows:

The contact surface pressure (refers to as "Pressure") in the third elastic region 41 is higher than that in the second elastic region 40;

"Pressure" in the second elastic region 40 is higher than or equal to that in the first elastic region 39; and "Pressure" in the first elastic region 39 is higher than that in the fourth elastic region 42. It will also be understood from TABLE 1 that levels of the contact surface pressure in the respective elastic regions of Example, except the fourth elastic region 42, are relatively high in comparison with the corresponding regions of the Comparative Example. Therefore, the diaper of Example fits, in use, better to the body of the wearer than the diaper of Comparative Example.

The aspects of the present invention described above may be arranged in at least the following items:

(i) a disposable diaper (10) having a longitudinal axis (P) and a transverse axis (Q) extending orthogonally to the longitudinal axis, a skin-facing side and a non-skin-facing-side opposite to the skin-facing side, and comprising a first waist region (13), a second waist region (14), a crotch region (15) extending between the first and second waist regions, a waist-opening (16) and a pair of leg-openings (17a, 17b), wherein:

at least the first waist region of the first and second waist regions is elastically contractible;

the first waist region is provided between opposite side edges (18c, 18c) thereof with at least one waist auxiliary elastic sheet (24A, 24B) extending in a direction of the transverse axis and leg auxiliary elastic sheets (26A, 26B) extending along front peripheral edges of the leg-openings;

the at least one waist auxiliary elastic sheet and the leg auxiliary elastic sheets directly or indirectly overlap one another at regions (41) defined between the opposite side edges of the first waist region in vicinities of the leg-openings.

The respective regions overlapping one another are preferably adapted to be positioned so as to come in contact with upper lateral regions of the wearer's iliac bone and/or the vicinity thereof as the diaper is worn.

The aspect of the present invention described in the above item (i) may provide one or more of the following advantageous effect(s):

(a) In the disposable diaper, at least in the first waist region, the at least one waist auxiliary elastic sheet and the leg auxiliary elastic sheets directly or indirectly overlap one another in the areas of the opposite side edges of the first waist region in vicinities of the leg-openings. With the diaper put on the wearer's body, these areas come in contact with upper lateral regions of the wearer's iliac bones inclusive of the vicinity thereof. In this way, the diaper is assured to be locally put in close contact with wearer's body and to be prevented from undesirable displacement.

Additionally, one or more of the following embodiments are provided in accordance with further aspects:

(ii) The diaper the first waist region further includes a non-elastic sheet (23) lying on the non-skin-facing side and an elastic sheet (22) lying on the skin-facing side, wherein the at least one waist auxiliary elastic sheet is sandwiched between the non-elastic sheet and the elastic sheet, and the leg auxiliary elastic sheets are attached to the skin-facing side of the elastic sheet.

(iii) The first waist region further includes a non-elastic sheet (23) lying on the non-skin-facing side and an elastic sheet (22) lying on the skin-facing side, wherein both of the at least one waist auxiliary elastic sheet and the leg auxiliary elastic sheets are sandwiched between the non-elastic sheet and the elastic sheet.

(iv) The first waist region comprises at least one first elastic region (39) in which the at least one waist auxiliary elastic sheet is provided, second elastic regions (40) in which the leg auxiliary elastic sheets are provided, third elastic regions (41) in which the at least one waist auxiliary elastic sheet and the leg auxiliary elastic sheets directly or indirectly overlap one another, and a fourth elastic region (42) which extends along a peripheral edge of the waist-opening in the direction of the transverse axis and in which neither the at least one waist auxiliary elastic sheet nor the leg auxiliary elastic sheets are provided, wherein a contact surface pressure in the first-fourth elastic regions is correlated one with another as follows:

The contact surface pressure (refers to as "Pressure" in the third elastic regions is higher that that in the second elastic region;

"Pressure" in the second elastic region is higher than or equal to that in the first elastic region; and "Pressure" in the first elastic region is higher than that in the fourth elastic region.

(v) The diaper further comprises a liquid-absorbent core (35), and the at least one waist auxiliary elastic sheet comprises a pair of auxiliary elastic sheets provided in opposite lateral zones of the first waist region without overlapping opposite outer side edges of the liquid-absorbent core.

(vi) The pair of auxiliary elastic sheets are symmetric about the longitudinal axis (P).

(vii) The at least one waist auxiliary elastic sheet continuously extends in the direction of the transverse axis across opposite lateral zones of the first waist region in the direction of the transverse axis.

(viii) The contact surface pressure in the first elastic region is about 60 to 100 g/cm$^2$, the contact surface pressure in the second elastic region is about 70 to 120 g/cm$^2$, the contact surface pressure in the third elastic region is 140 to 230 g/cm$^2$, and the contact surface pressure in the fourth elastic region is about 30 to 70 g/cm$^2$.

(ix) A width dimension of said waist auxiliary elastic sheets is greater than a width dimension of said leg auxiliary elastic sheets.

(x) A width dimension of the at least one waist auxiliary elastic sheets is 10 mm or larger, and a width dimension of the leg auxiliary elastic sheets is about 5 mm or larger.

(xi) The width dimension of the at least one waist auxiliary elastic sheet is at least 50% of a length dimension, in a direction of the longitudinal axis, of the side edges (18c) of the first waist region.

(xii) The width dimension of the leg auxiliary elastic sheets is 5 mm or larger at least in the regions (41) where the leg auxiliary elastic sheets overlap with the at least one waist auxiliary elastic sheet.

(xiii) The width dimension of the leg auxiliary elastic sheets is tapered from the respective side edges (18c) of the first waist region toward the crotch region.

(xiv) The elastic sheet comprises a non-woven fabric of mixed fibers including elastomer fibers and thermoplastic fibers which are neither elastically stretchable nor elastically contractible, and the elastomer fibers have a mixing rate in a range of 20 to 75% by mass of all mixed fibers of the non-woven fabric.

(xv) Both first and second waist regions are elastically contractible, and each comprise the at least one waist auxiliary elastic sheet and the leg auxiliary elastic sheets overlapping one another at the regions adapted to come in contact with upper lateral regions of a wearer's iliac bones and a vicinity thereof when the diaper is worn by the wearer.

According to the embodiments in the above (ii) to (xv), one or more of the advantageous effect(s) set forth at (a) is/are better ensured. Further advantageous effects of the respective embodiments may be obtained as discussed in the respective descriptions.

As used herein, the terms "first", "second", "third" and "fourth" are use merely for distinguishing between similar elements. Furthermore, as used herein, the wording "first waist region" means one of the front and rear waist regions, and the wording "second waist region" means the other.

The invention claimed is:

1. A disposable diaper having a longitudinal axis and a transverse axis extending orthogonally to the longitudinal axis, a skin-facing side and a non-skin-facing-side opposite to said skin-facing side, said disposable diaper comprising:

a first waist region, a second waist region, a crotch region extending between said first and second waist regions, a waist-opening and a pair of leg-openings, wherein at least said first waist region of said first and second waist regions is elastically contractible;

an absorbent chassis bonded to said first and second waist regions and extending between said first and second waist regions;

at least one waist auxiliary elastic sheet provided in the first waist region between opposite side edges thereof and extending in a direction of said transverse axis; and leg auxiliary elastic sheets provided in the first waist region and extending along front peripheral edges of said leg-openings, wherein said at least one waist auxiliary elastic sheet and said leg auxiliary elastic sheets directly or indirectly overlap one another in a thickness direction of the disposable diaper, when the disposable diaper is laid flat in a flatly developed state with longitudinal ends spaced full away from one another, at regions including intersections of (i) said opposite side edges of said first waist region and (ii) the front peripheral edges of said leg-openings, said first waist region includes:
- at least one first elastic region including said at least one waist auxiliary elastic sheet,
- second elastic regions including said leg auxiliary elastic sheets,
- third elastic regions in which said at least one waist auxiliary elastic sheet and said leg auxiliary elastic sheets directly or indirectly overlap one another, and
- a fourth elastic region extending along a peripheral edge of said waist-opening in the direction of said transverse axis and free of said at least one waist auxiliary elastic sheet and said leg auxiliary elastic sheets, contact surface pressures in said first, second, third and fourth elastic regions are correlated one with another in the following relationship:
- the contact surface pressure in the third elastic region is higher than that in the second elastic region;
- the contact surface pressure in the second elastic region is higher than or equal to that in the first elastic region; and
- the contact surface pressure in the first elastic region is higher than that in the fourth elastic region, said absorbent chassis comprises an inner sheet, an outer sheet, and a liquid-absorbent core sandwiched between said inner sheet and said outer sheet, said inner and outer sheets extend outward beyond side edges of said liquid-absorbent core and are bonded together to define a pair of side flaps extending in a direction of said longitudinal axis, and in a plan view of the disposable diaper in the flatly developed state, said at least one waist auxiliary elastic sheet intersects with one of said side flaps but not with said side edges of said liquid-absorbent core.

2. The diaper defined by claim 1, wherein said first waist region further includes a non-elastic sheet lying on said non-skin-facing side and an elastic sheet lying on said skin-facing side, said at least one waist auxiliary elastic sheet is sandwiched between said non-elastic sheet and said elastic sheet, and said leg auxiliary elastic sheets are attached to said skin-facing side of said elastic sheet.

3. The diaper defined by claim 1, wherein said first waist region further includes a non-elastic sheet lying on said non-skin-facing side and an elastic sheet lying on said skin-facing side, and both of said at least one waist auxiliary elastic sheet and said leg auxiliary elastic sheets are sandwiched between said non-elastic sheet and said elastic sheet of the first waist region.

4. The diaper defined by claim 1, wherein said at least one waist auxiliary elastic sheet continuously extends in the direction of said transverse axis across opposite lateral zones of said first waist region in the direction of said transverse axis.

5. The diaper defined by claim 1, wherein the contact surface pressure in said first elastic region is 60 to 100 g/cm$^2$, the contact surface pressure in said second elastic region is 70 to 120 g/cm$^2$, the contact surface pressure in said third elastic region is 140 to 230 g/cm$^2$, and the contact surface pressure in said fourth elastic region is 30 to 70 g/cm$^2$.

6. The diaper defined by claim 1, wherein a width dimension of said at least one waist auxiliary elastic sheet is greater than a width dimension of said leg auxiliary elastic sheets.

7. The diaper defined by claim 1, wherein a width dimension of said at least one waist auxiliary elastic sheet is 10 mm or larger, and a width dimension of said leg auxiliary elastic sheets is 5 mm or larger.

8. The diaper defined by claim 1, wherein a width dimension of said at least one waist auxiliary elastic sheet is at least 50% of a length dimension, in the direction of the longitudinal axis, of the side edges of the first waist region.

9. The diaper defined by claim 1, wherein a width dimension of said leg auxiliary elastic sheets is 5 mm or larger at least in the regions where the leg auxiliary elastic sheets overlap with the at least one waist auxiliary elastic sheet.

10. The diaper defined by claim 8, wherein the width dimension of said leg auxiliary elastic sheets is tapered from the respective side edges of the first waist region toward the crotch region.

11. The diaper defined by claim 2, wherein the elastic sheet of the first waist region comprises a non-woven fabric of mixed fibers including elastomer fibers and thermoplastic fibers which are neither elastically stretchable nor elastically contractible, and the elastomer fibers have a mixing rate in a range of 20 to 75% by mass of all mixed fibers of the non-woven fabric.

12. The diaper defined by claim 1, wherein both said first and second waist regions are elastically contractible, and each comprise said at least one waist auxiliary elastic sheet and said leg auxiliary elastic sheets overlapping one another at the regions adapted to come in contact with upper lateral regions of a wearer's iliac bones and a vicinity thereof when the diaper is worn by the wearer.

13. The diaper defined by claim 1, wherein said regions where said at least one waist auxiliary elastic sheet and said leg auxiliary elastic sheets directly or indirectly overlap one another further includes said opposite side edges of said first waist region and the front peripheral edges of said leg-openings.

14. The diaper defined by claim 1, wherein said at least one waist auxiliary elastic sheet and said leg auxiliary elastic sheets intersect each other at intersections of said opposite side edges of said first waist region and the front peripheral edges of said leg-openings.

15. The diaper defined by claim 1, wherein the leg auxiliary elastic sheets are curved when the diaper is laid flat in the flatly developed state.

16. The diaper defined by claim 1, wherein, when the disposable diaper is laid flat in the flatly developed state, the leg auxiliary elastic sheets extend from a direction generally parallel to the longitudinal axis to a direction generally perpendicular to the longitudinal axis.

17. A disposable diaper having a longitudinal axis and a transverse axis extending orthogonally to the longitudinal axis, a skin-facing side and a non-skin-facing-side opposite to said skin-facing side, said disposable diaper comprising:

a first waist region, a second waist region, a crotch region extending between said first and second waist regions, a waist-opening and a pair of leg-openings, wherein at least said first waist region of said first and second waist regions is elastically contractible;

at least one waist auxiliary elastic sheet provided in the first waist region between opposite side edges thereof and extending in a direction of said transverse axis; and leg auxiliary elastic sheets provided in the first waist region and extending along front peripheral edges of said leg-openings, wherein said at least one waist auxiliary elastic sheet and said leg auxiliary elastic sheets directly or indirectly overlap one another in a thickness direction of the disposable diaper when the disposable diaper is laid flat with longitudinal ends spaced full away from one another at regions including intersections of (i) said opposite side edges of said first waist region and (ii) the front peripheral edges of said leg-openings, said first waist region includes:
- at least one first elastic region including said at least one waist auxiliary elastic sheet,
- second elastic regions including said leg auxiliary elastic sheets,
- third elastic regions in which said at least one waist auxiliary elastic sheet and said leg auxiliary elastic sheets directly or indirectly overlap one another, and
- a fourth elastic region extending along a peripheral edge of said waist-opening in the direction of said transverse axis and free of said at least one waist auxiliary elastic sheet and said leg auxiliary elastic sheets, and contact surface pressures in said first, second, third and fourth elastic regions are correlated one with another in the following relationship:
- the contact surface pressure in the third elastic region is higher than that in the second elastic region;
- the contact surface pressure in the second elastic region is higher than or equal to that in the first elastic region; and
- the contact surface pressure in the first elastic region is higher than that in the fourth elastic region, wherein
said first waist region further includes a non-elastic sheet lying on said non-skin-facing side and an elastic sheet lying on said skin-facing side, and both of said at least one waist auxiliary elastic sheet and said leg auxiliary elastic sheets are sandwiched between said non-elastic sheet and said elastic sheet of the first waist region.

18. The diaper defined by claim 1, wherein
said at least one waist auxiliary elastic sheet comprises two waist auxiliary elastic sheets, and
the absorbent core is located between said two waist auxiliary elastic sheets in the direction of said transverse axis.

19. The diaper defined by claim 18, wherein, in the plan view of the disposable diaper in the flatly developed state, said two waist auxiliary elastic sheets overlap the corresponding side flaps of the absorbent chassis in the thickness direction but do not overlap any of the side edges of the absorbent core in the thickness direction.

* * * * *